United States Patent
Hiller et al.

(10) Patent No.: US 10,751,534 B2
(45) Date of Patent: Aug. 25, 2020

(54) SYSTEMS AND METHODS FOR OBESITY DIAGNOSIS AND/OR TREATMENT

(71) Applicants: Boston Scientific Scimed, Inc., Maple Grove, MN (US); Lifespan Corporation, Providence, RI (US)

(72) Inventors: Jeri Ann Hiller, Westford, MA (US); Peter J. Snyder, East Greenwich, RI (US); Gene Thomas Storbeck, Franklin, MA (US); Kali Manning, Providence, RI (US); Selina M. Mello, New Brighton, MN (US); Holly Elizabeth Rockweiler, San Francisco, CA (US); John Allen Hingston, Framingham, MA (US); Ding Sheng He, Tyngsboro, MA (US); Dawn Winsor-Hines, Northborough, MA (US); Harlan Rich, Providence, RI (US); Kathleen Corcoran, Watertown, MA (US); Gary Dean Roye, Cranston, RI (US); Beth Ryder, Warwick, RI (US); Sivamainthan Vithiananthan, Sharon, MA (US)

(73) Assignees: Boston Scientific Scimed, Inc., Maple Grove, MN (US); Lifespan Corporation, Providence, RI (US)

( * ) Notice: Subject to any disclaimer, the term of this patent is extended or adjusted under 35 U.S.C. 154(b) by 270 days.

(21) Appl. No.: 15/789,025

(22) Filed: Oct. 20, 2017

(65) Prior Publication Data
US 2018/0110979 A1   Apr. 26, 2018

Related U.S. Application Data

(60) Provisional application No. 62/412,001, filed on Oct. 24, 2016.

(51) Int. Cl.
*A61N 1/36* (2006.01)
*A61B 5/00* (2006.01)
(Continued)

(52) U.S. Cl.
CPC ...... *A61N 1/36007* (2013.01); *A61B 5/04884* (2013.01); *A61B 5/4238* (2013.01);
(Continued)

(58) Field of Classification Search
CPC ............... A61N 1/36007; A61N 1/378; A61B 5/04884; A61B 5/4238; A61B 5/4255;
(Continued)

(56) References Cited

U.S. PATENT DOCUMENTS 6,427,089 B1 * 7/2002 Knowlton .............. A61B 18/18
                                                          607/101
7,160,254 B2   1/2007 Noar
(Continued)

OTHER PUBLICATIONS

Thomas L. Abell et al., "Glucagon-Evoked Gastric Dysrhythmias in Humans Shown by an Improved Electrogastrographic Technique Gastroenterology", Gastroenterology, 1985; vol. 88: pp. 1932-1940.
(Continued)

*Primary Examiner* — Lindsey G Wehrheim
(74) *Attorney, Agent, or Firm* — Bookhoff McAndrews, PLLC

(57) ABSTRACT

A system for treating a gastrointestinal tract may include a device configured to measure electrical activity at a plurality of locations within a gastrointestinal tract of a patient, a controller configured to compare the measured activity from the plurality of locations to a database of electrical activity corresponding to one or more gastric events, abnormalities, or dysrhythmias. The controller may be configured to deter-
(Continued)

mine one or more treatment locations based on the comparison, and cause the device to deliver therapy to the one or more treatment locations.

20 Claims, 10 Drawing Sheets

(51) Int. Cl.

| | |
|---|---|
| *A61N 1/378* | (2006.01) |
| *A61B 18/14* | (2006.01) |
| *A61B 5/0488* | (2006.01) |
| *A61B 5/0245* | (2006.01) |
| *A61B 18/00* | (2006.01) |
| *A61B 90/00* | (2016.01) |

(52) U.S. Cl.
CPC .......... *A61B 5/4255* (2013.01); *A61B 5/4283* (2013.01); *A61B 18/1477* (2013.01); *A61N 1/378* (2013.01); *A61B 5/0245* (2013.01); *A61B 5/4227* (2013.01); *A61B 5/4869* (2013.01); *A61B 5/6843* (2013.01); *A61B 5/6844* (2013.01); *A61B 5/6852* (2013.01); *A61B 5/6871* (2013.01); *A61B 5/6873* (2013.01); *A61B 18/1492* (2013.01); *A61B 2018/0022* (2013.01); *A61B 2018/00023* (2013.01); *A61B 2018/00267* (2013.01); *A61B 2018/00494* (2013.01); *A61B 2018/00577* (2013.01); *A61B 2018/00839* (2013.01); *A61B 2090/065* (2016.02)

(58) Field of Classification Search
CPC .............. A61B 5/4283; A61B 18/1477; A61B 2090/065; A61B 5/0245; A61B 5/4227; A61B 5/4869; A61B 5/6843; A61B 5/6844; A61B 5/6852; A61B 5/6871; A61B 5/6873; A61B 18/1492; A61B 2018/00023; A61B 2018/0022; A61B 2018/00267; A61B 2018/00494; A61B 2018/00577; A61B 2018/00839
See application file for complete search history.

(56) References Cited

U.S. PATENT DOCUMENTS

| | | | |
|---|---|---|---|
| 7,165,551 B2 | 1/2007 | Edwards et al. | |
| 7,252,665 B2 | 8/2007 | Starkebaum et al. | |
| 7,326,207 B2 | 2/2008 | Edwards | |
| 2002/0165589 A1* | 11/2002 | Imran ................... | A61B 5/4238 607/40 |
| 2004/0215180 A1 | 10/2004 | Starkebaum et al. | |
| 2013/0035576 A1* | 2/2013 | O'Grady ............ | A61B 5/04884 600/373 |
| 2014/0058282 A1 | 2/2014 | O'Grady et al. | |
| 2015/0057519 A1 | 2/2015 | Ben-David et al. | |

OTHER PUBLICATIONS

O. Bayguinov et al., "Movement based artifacts may contaminate extracellular electrical recordings from GI muscles", Neurogastroenterol Motil., Nov. 2011; vol. 23. No. 11, 1029—e498, 29 pp.
Michael Camilleri, M.D., 2007, Clinical practice, "Diabetic gastroparesis", The New England Journal of Medicine, 356;8, Feb. 22, 2007, pp. 820-829.
Leo K. Cheng, "Slow wave conduction patterns in the stomach: from Waller's foundations to current challenges", Acta Physiol (Oxf), Feb. 2015, vol. 213, No. 2, pp. 384-393, 18 pp.

R. Coleski et al., 2009, "Coupling and propagation of normal and dysrhythmic gastric slow waves during acute hyperglycaemia in healthy humans", Neurogastroenterol Motil 21, pp. 492-499, e1-2.
R. Coleski et al., 2004, "Directed endoscopic mucosal mapping of normal and dysrhythmic gastric slow waves in healthy humans", Neurogastroenterol Motil 16, pp. 557-565.
Edward A. Fox, "Treating Diet-Induced Obesity: A New Role for Vagal Afferents?," Department of Psychological Sciences Faculty Publications, Paper 18, 2012.
S.J. French et al., "Preliminary studies on the gastrointestinal responses to fatty meals in obese people", International Journal of Obesity 17, pp. 295-300, 1993.
G.L. Rapaccini et al., "Gastric Wall Thickness in Normal and Neoplastic Subjects: A Prospective Study Performed by Abdominal Ultrasound," Gastrointest Radiol 13, Pp. 197-199, 1988.
B. Glasbrenner, "Gastric emptying of solids and liquids in obesity", The Clinical Investigator, vol. 71, No. 7, pp. 542-546, 1993.
Per Grybäck et al., "Gastric emptying of solids in humans: Improved evaluation by Kaplan-Meier plots, with special reference to obesity and gender", European Journal of Nuclear Medicine, vol. 23, No. 12, pp. 1562-1567, 1996.
Xinfu Guan et al., "GLP-2 receptor in POMC neurons suppresses feeding behavior and gastric motility", Am J Physiol Endocrinol Metab., Oct. 1, 2012, vol. 303. No. 7, pp. E853-E864, 12 pp.
Hans-Rudolf Berthoud, "The Vagus Nerve, Food Intake and Obesity," Regul Pept., vol. 149, No. 1-3, pp. 15-25, 2008.
John W. Hamilton et al., Human Electrogastrograms, "Comparison of surface and Mucosal Recordings", Digestive Diseases and Sciences, vol. 31, No. 1, Jan. 1986, pp. 33-39.
M. Horowitz, "Abnormalities of Gastric Emptying in Obese Patients", International Journal of Obesity, vol. 7, pp. 415-421, Sep. 30, 1983.
Hutson WR et al., "Obesity and weight reduction do not influence gastric emptying and antral motility", The American Journal of Gastroenterology, vol. 88, No. 9, pp. 1405-1409, Sep. 1993.
John G. Kral, "Truncal vagotomy in morbid obesity", International Journal of Obesity, vol. 5, pp. 431-435, 1981.
Wim J. E. P. Lammers et al., 2008, "Focal Activities and Re-Entrant Propagations as Mechanisms of Gastric Tachyarrhythmias" Gastroenterology 135, pp. 1601-1611.
A. Maddox, "Gastric and oesophageal emptying in obesity", Scandinavian Journal of Gastroenterology, vol. 24, No. 5, pp. 593-598, 1989.
E. M. H. Mathus-Vliegen, MD, PhD et al., "Gastric emptying, CCK release, and satiety in weight-stable obese subjects", Digestive Diseases and Sciences, vol. 50, No. 1, Jan. 2005, pp. 7-14.
Erik Näslund, MD, PhD et al., "Distal Small Bowel Hormones: Correlation with Fasting Antroduodenal Motility and Gastric Emptying," Digestive Diseases and Sciences, vol. 43, No. 5, pp. 945-952, May 1998.
Gregory O'Grady et al., Sep. 2011, "High-resolution spatial analysis of slow wave initiation and conduction in porcine gastric dysrhythmia", Neurogastroenterol Motil., vol. 23, No. 9, e345—e355.
Gregory O'Grady et al., 2012, "Abnormal Initiation and Conduction of Slow-Wave Activity in Gastroparesis, Defined by High-Resolution Electrical Mapping", 17 pp., Gastroenterology, vol. 143, No. 3, 589-598.e3.
Gregory O'Grady et al., 2010, "Origin and propagation of human gastric slow-wave activity defined by high-resolution mapping", Am J Physiol Gastrointest Liver Physiol 299, G585-G592.
Robert J. Phillips et al., "Regenerating Vagal Afferents Reinnervate Gastrointestinal Tract Smooth Muscle of the Rat," The Journal of Comparative Neurology, vol. 421, pp. 325-346, 2000.
Robert F. Kushner, "Evaluation and Management of Obesity," in Harrison's Principles of Internal Medicine, 18 ed: McGraw-Hill, 2012, pp. 629-636.
Poong-Lyul Rhee et al., 2011, "Analysis of pacemaker activity in the human stomach", J Physiol 589.24, pp. 6105-6118.
A. T. Stearns, "Relative Contributions of Afferent Vagal Fibers to Resistance to Diet-Induced Obesity," Dig Dis Sci, vol. 57, No. 5, pp. 1281-1290, May 2012.
Tosetti C et al., "Gastric emptying of solids in morbid obesity", International Journal of Obesity and related metabolic disorders,

(56) References Cited

OTHER PUBLICATIONS

Journal of the International Association for the Study of Obesity, vol. 20, No. 3. pp. 200-205, 9 pp., Mar. 1996.
C Verdich et al., "Effects of obesity and major weight reduction on gastric emptying", International Journal of Obesity 24, pp. 899-905, 2000.
Richard A. Wright et al., "Gastric emptying and obesity", Gastroenterology, vol. 84, No. 4, pp. 747-751, 1983.
Chul H. You et al., "Electrogastrographic Study of Patients with Unexplained Nausea, Bloating, and Vomiting", Gastroenterology 79, Aug. 1980, pp. 311-314.
Zahorska-Markiewicz B et al., "Gastric emptying in obesity", Human Nutrition: Clinical Nutrition, vol. 40C, No. 3, pp. 309-313, May 1986.

\* cited by examiner

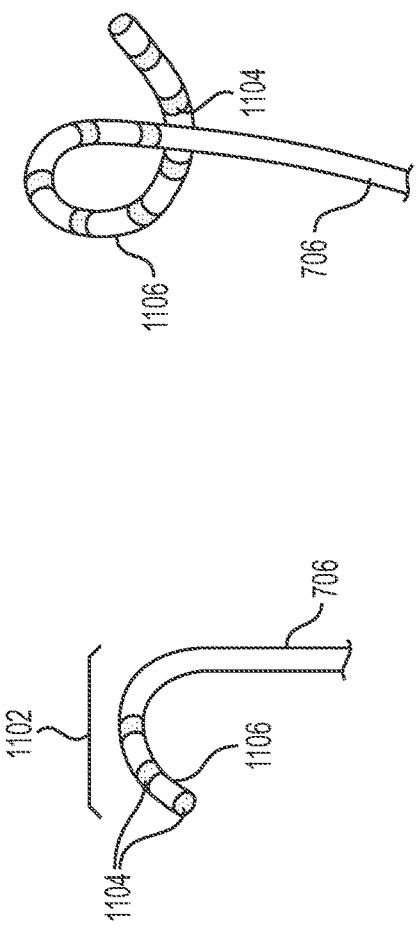
FIG. 11
FIG. 12
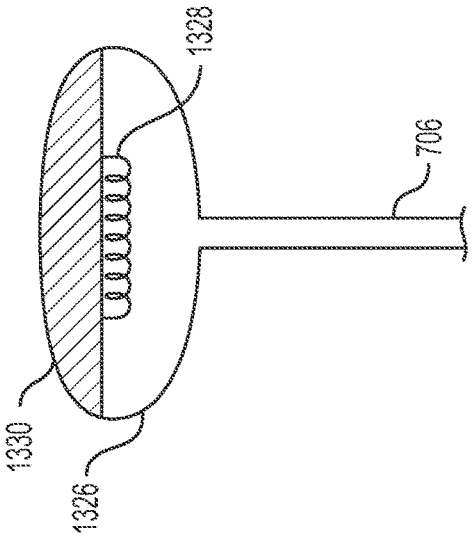
FIG. 13
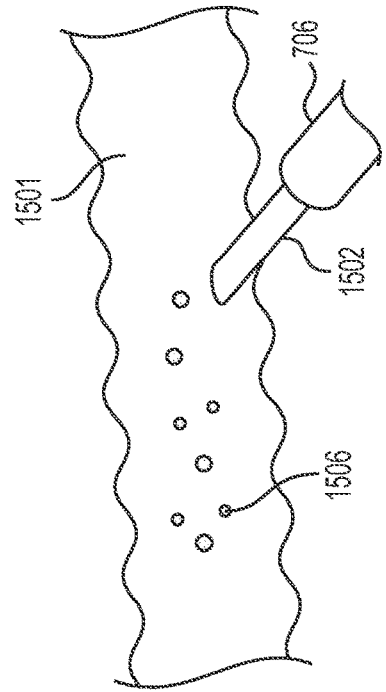
FIG. 14
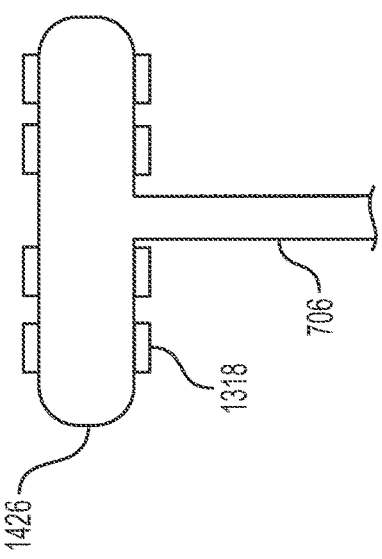
FIG. 15

SYSTEMS AND METHODS FOR OBESITY DIAGNOSIS AND/OR TREATMENT

CROSS-REFERENCE TO RELATED APPLICATIONS

This application claims the benefit under 35 U.S.C § 119(e) of U.S. Provisional Application No. 62/412,001, filed on Oct. 24, 2016, the entirety of which is incorporated by reference herein.

TECHNICAL FIELD

Various examples of the present disclosure relate generally to systems and methods for obesity diagnosis and/or treatment.

BACKGROUND

Obesity is a growing epidemic with approximately two-thirds of the American population being overweight or obese. Obesity is a state of excess adiposity, and the current treatment options include lifestyle modification, pharmacotherapy, and bariatric surgery. Lifestyle modification is only effective for five percent of those who try it, pharmacotherapy is limited in efficacy in addition to adverse side effects, and bariatric surgery qualification is rigorous, resulting in a very small patient pool that end up receiving surgery.

Scintigraphy and MRI provide evidence of disrupted motility patterns in the gastrointestinal (GI) tract, but they do not elucidate the underlying electrical patterns of the stomach, and thus do not explain why and how these patterns occur. Direct measurement of myoelectric activity is possible by the placement of serosal electrodes on the stomach, but this requires open surgery or laparotomy. Prior attempts to record gastric activity with mucosal electrodes have had limited success due to easy dislodgement, the inability to be directed to specific regions in the stomach, and a limited number of available electrodes on existing devices. Furthermore, the clinical application of therapies that rely on mapping the stomach has not been realized due to the deficiencies noted above. Additionally, there is no strong clinical data to provide insight into how stomach dysrhythmias may contribute to conditions such as obesity.

Many patients indicate a lack of satiety before bariatric surgery. Gastric dysrhythmia may be a contributing cause of obesity. For example, accelerated gastric emptying of solids (among other mechanisms of action) could be linked to the feeling of a lack of satiety, because food may not stay in the stomach for long enough to sufficiently signal satiety. A link also has been made between faster gastric emptying and increased food intake. However, data substantiating this link is inconsistent. Delayed gastric empting is also linked to obesity. Abnormal gastric motility may be linked to obesity by differing mechanisms of action. Medical practitioners are also unable to accurately predict the efficacy of certain obesity treatments before treatments are performed.

Thus, there remains a need for a GI mapping tool, and treatment options that are acceptable to a large potential patient pool.

SUMMARY OF THE DISCLOSURE

In one aspect, the present disclosure is directed to a system for treating a gastrointestinal tract. The system may include a device configured to measure electrical activity at a plurality of locations within a gastrointestinal tract of a patient, a controller configured to compare the measured activity from the plurality of locations to a database of electrical activity corresponding to one or more gastric events, abnormalities, or dysrhythmias. The controller may be configured to determine one or more treatment locations based on the comparison, and cause the device to deliver therapy to the one or more treatment locations.

The device may include a plurality of sensing elements that are longitudinally and circumferentially spaced apart from one another, wherein each of the plurality of sensing elements may be configured to measure electrical activity from one of the plurality of locations within the gastrointestinal tract. Each of the plurality of sensing elements may be an electrode configured to deliver radiofrequency energy. Determining the one or more treatment locations may include selecting one or more of the plurality of sensing elements to deliver radiofrequency energy to the gastrointestinal tract. Causing the device to deliver therapy to the one or more treatment locations may include delivering radiofrequency energy to tissue with only the one or more selected sensing elements of the plurality of sensing elements. The device may be configured to measure a force applied by each of the plurality of sensing elements against a wall of the stomach. The controller may be configured to compare the measured force applied by each of the plurality of sensing elements to a threshold force level. The controller may compare the measured electrical activity from the plurality of locations to the database of electrical activity only when the force applied by each of the plurality of sensing elements is above the threshold force level. The controller may be configured to provide an indication that the device should be expanded to a greater extent when the force applied by one or more of the plurality of sensing elements is below the threshold force level. The system may include a fluid delivery system configured to cool a volume of liquid, wherein the device may include a balloon, and the fluid delivery system may be configured to deliver the cooled liquid to inflate the balloon. The one or more gastric events, abnormalities, or dysrhythmias may include an origin of a slow wave. The database may include patterns of simulated electrical activity. The database may include electrical activity recorded from other patients. The controller may be configured to receive the database, over an electronic network, from a server. The server may be configured to receive electrical data measured by different expandable devices via the electronic network, and may be configured to update the database after receiving electrical data from the different expandable devices.

In another aspect, the present disclosure is directed to a method of treating a gastrointestinal system. The method may include creating an opening through a wall of a stomach, positioning an energy delivery device from an interior of the stomach, through the opening, to an exterior of the stomach. The method also may include delivering energy from the energy delivery device to an exterior surface of the stomach to reduce the ability of the stomach to expand or contract.

Delivering energy may damage smooth muscle tissue of the stomach. Delivering energy may damage nerve tissue that at least partially controls the ability of the stomach to expand or contract.

In yet another aspect, the present disclosure is directed to a method of treating a gastrointestinal system. The method may include applying energy from an energy delivery device to damage stomach tissue to reduce the ability of the stomach to expand or contract without damaging a mucosal surface disposed inside the stomach.

The method may include actively cooling the mucosal surface while applying energy.

BRIEF DESCRIPTION OF THE FIGURES

The accompanying drawings, which are incorporated in and constitute a part of this specification, illustrate various examples and together with the description, serve to explain the principles of the disclosed examples.

FIGS. 10-14 are side views of devices according to various examples of the present disclosure.

FIG. 15 is a schematic view of a delivery system, according to an example of the present disclosure.

DETAILED DESCRIPTION

Reference will now be made in detail to examples of the present disclosure, examples of which are illustrated in the accompanying drawings. Wherever possible, the same reference numbers will be used throughout the drawings to refer to the same or like parts.

Diagnostic tools of the present disclosure may be used to identify patients with gastric motility dysrhythmias that may contribute to their obesity. Upon diagnosis, medical practitioners may be able to provide these patients with personalized obesity treatment(s). These personalized treatments may increase a patient's ability to lose weight. Devices and methods of the present disclosure also may be used as higher resolution diagnostic tools for broader applications, such as, e.g., diagnosing and/or treating nausea and gastroparesis.

These higher resolution research tools and/or diagnostic tools could be used to identify reproducible dysrhythmias in obese patients, and potentially link dysrhythmias to different obesity conditions. This information can be used to develop personalized treatments with improved outcomes. The use of diagnostic mapping tools in clinical studies in obese patients may help identify subpopulations of patients with different myoelectric activity profiles.

Devices and methods of the present disclosure also may help determine whether ectopic pacemakers can arise in the gastrointestinal (GI) tract, and whether they can be the origin of GI motility disorders, as arrhythmic patterns in the GI tract may be similar to those in the heart. The disclosed tools and methods may enable the development and use of minimally invasive devices to treat obesity, diabetes, and gastric motility disorders. In addition, devices and methods of the present disclosure may help educate patients, and provide medical practitioners with higher confidence in treatment outcomes. Devices and methods of the present disclosure may help determine medications to correct patient dysrhythmias, or identify endoscopic therapies that specifically alter myoelectric patterns and/or gastric emptying.

The stomach functions in digestion via physical and chemical degradation of ingested food. Chemical digestion occurs due to the various enzymes and substances released from the gastric pits located in the mucosa. Physical digestion occurs due to the coordinated frequent contractions of the stomach muscles called peristalsis, which crushes food. The joined physical and chemical degradation is necessary for proper absorption of nutrients. Inhibiting stomach function would decrease the amount of consumed food that is absorbed.

Figure 1:
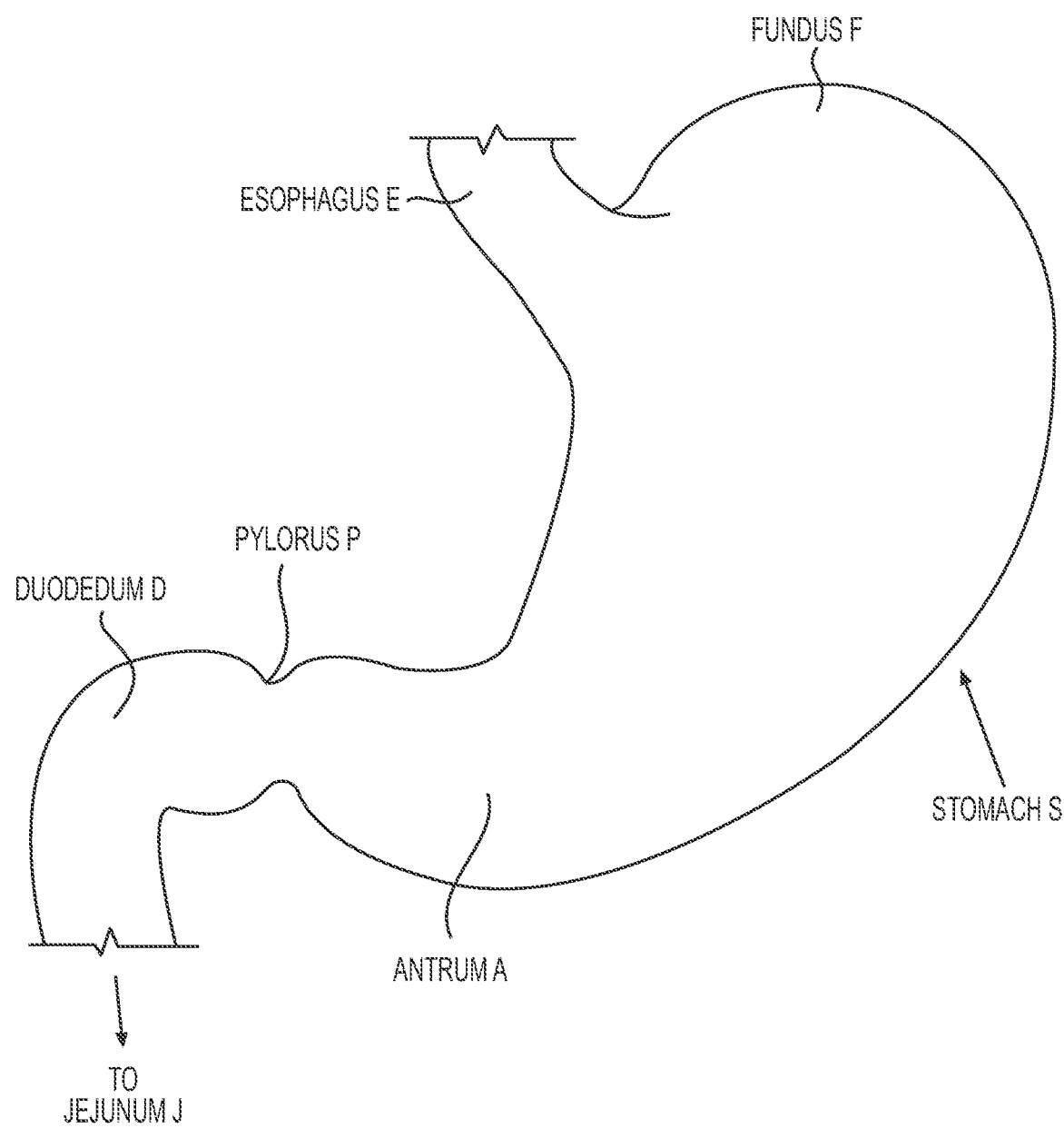
FIG. 1 is a schematic view illustration of a gastrointestinal system.

FIG. 1 depicts a schematic view of a stomach and the surrounding gastrointestinal structures. An esophagus E is shown leading to a Stomach S. Stomach S includes a fundus F at its proximal end and an antrum A at its distal end. Antrum A feeds into the pylorus P, which attaches to the duodenum D at the proximal region of the small intestine. The middle region of the small-intestine, positioned distally of the duodenum D, is the jejunum J.

Figure 2:
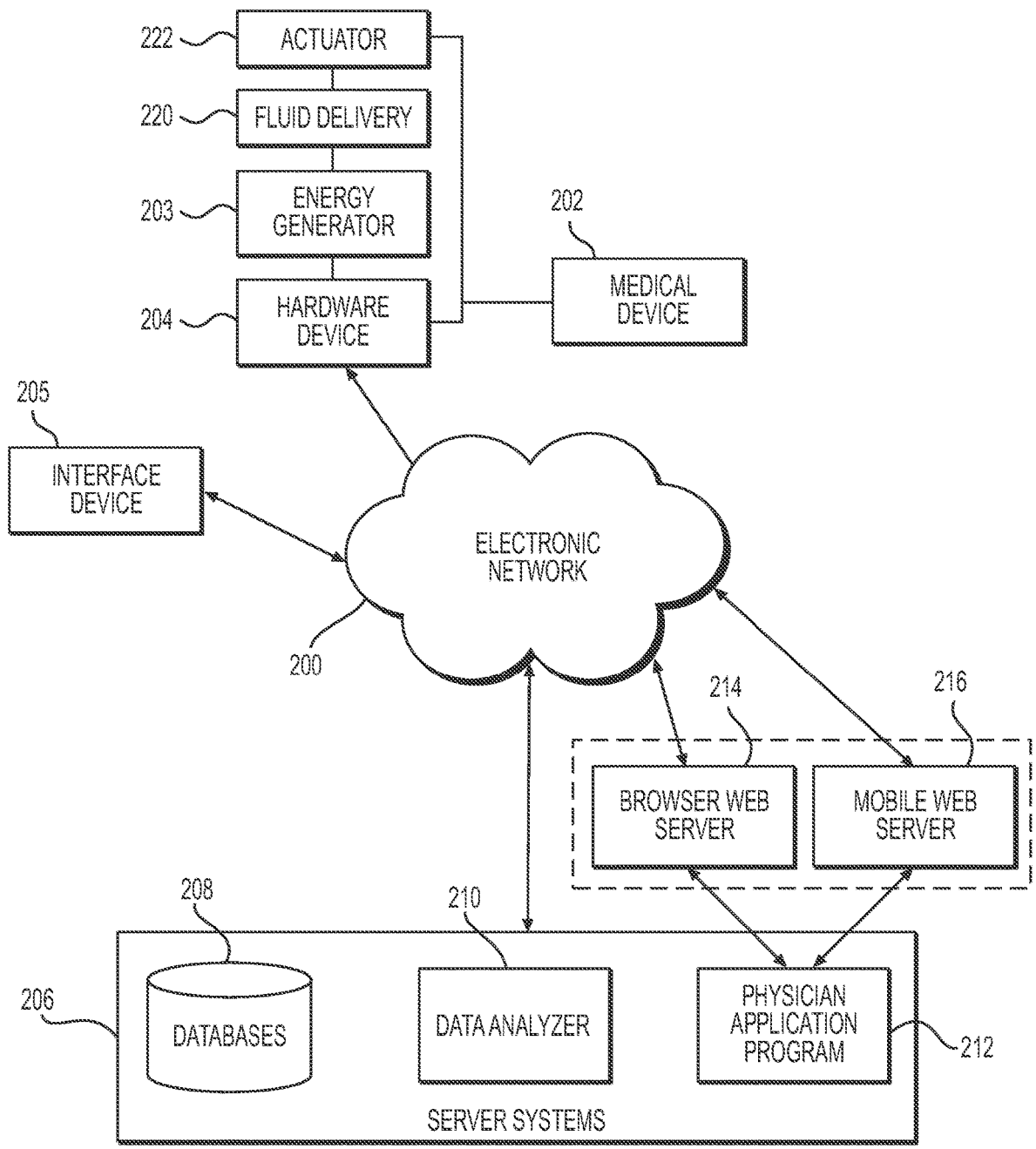
FIG. 2 is a schematic view illustration of a system, according an example of the present disclosure.

FIG. 2 is a schematic diagram of a system and environment for collecting, processing, and displaying electrical data obtained endoscopically from within the stomach or other portion of the GI tract, and for treating obesity conditions, according to an example of the present disclosure. As shown in FIG. 2, the system and environment may include one or more medical devices 202, hardware devices 204, and interface devices 205 disposed in communication with an electronic network 200. FIG. 2 depicts one of each of medical device 202, hardware device 204, and interface device 205. It is understood, however, that any number of medical devices 202, and associated hardware devices 204 and interface devices 205 may be used in the system. Each hardware device 204 and/or medical device 202 may be coupled to an energy generator 203, a fluid delivery system 220, and an actuator 222. The medical devices 202, hardware devices 204, interface devices 205, energy generators 203, fluid delivery systems 220, and actuators 222 comprise the portions of the system that a physician or other medical practitioner interacts with. This disclosure first describes these aspects of the system, followed by disclosure of the remainder of the system, including the servers, and exemplary methods of use.

Medical Devices

Various mapping devices are shown in FIGS. 3-6 that may comprise a portion of medical device 202. The various mapping devices may each include a catheter 302 that extends from a proximal end (not shown) toward a distal end 304.

Figure 3:
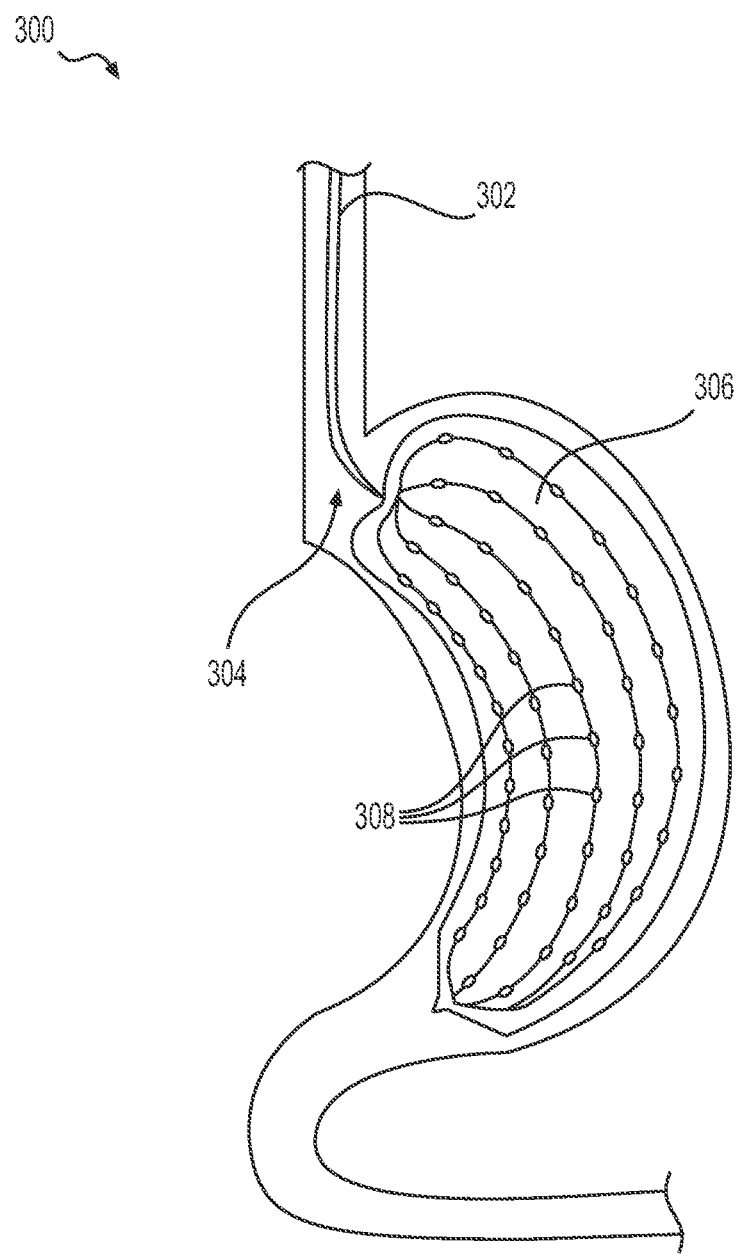
FIGS. 3-7 are schematic views of medical devices according to various examples of the present disclosure.

A mapping device 300 is shown in FIG. 3 having an expandable member (e.g., a balloon) 306, and a plurality of sensing elements 308. For example, expandable member 306 may include a balloon formed from a highly expandable and/or compliant material, such as, e.g., silicone. The material may allow the balloon to expand and conform to the shape of the stomach. As the pressure of the expandable member 306 is gradually increased, any folds in the gastric lining may straighten or flatten. This straightening or flattening may permit the sensing elements 308 on the surface of the expandable member 306 to come in contact with the stomach wall. A medical practitioner may control the pressure between the sensing elements 308 and the stretched stomach by controlling the pressure applied to the expandable member 306. In other examples, the pressure of expandable member 306 may be automatically controlled by a controller, such as, e.g., hardware device 204, in response to pressure, force, or some other feedback.

The sensing elements 308 on the surface of expandable member 306 may be linked to hardware device 204 by any suitable mechanism, such as, e.g., a thin wire running along the medical device 202, for example, inside catheter 302.

Expandable member 306 may be any suitable size. In some examples, expandable member 306 may be large enough to map the entire stomach while disposed in only one position. In other examples, smaller expandable members 306 may be used. In these examples, the expandable member 306 may need to be repositioned one or more times in order to map an entirety of the stomach.

In some examples, the sensing elements 308 may be integrated onto the surface of the balloon via, e.g., printing, adhesive, or other suitable mechanisms. In another example, sensing elements 308 may be electrodes including a conductive ink. A suitable conductive ink can be composed of a binder or base, and a conductive filler dispersed in the binder. The binder can be composed of a flexible, compliant polymer (e.g., urethane), silicone, or another suitable biocompatible material configured to stretch with the expandable member 306 during device operation. The conductive filler may include particles that have a variety of different sizes, shapes, distributions, and/or concentrations within the binder. For example, the conductive filler may include both small and large conductive flakes. The conductive filler also may include conductive fibers, strands, spheres, rods, cylinders, strips, pellets, or combinations thereof. The individual particles or fibers of the conductive filler may be oriented to slide over one another (e.g., overlapping) to maintain contact as the corresponding conductive ink stretches and expands during operation so as to ensure conductive continuity and durability. The conductive filler may include silver, gold, copper, carbon, or other suitable biocompatible conductive materials.

In yet another example, sensing elements 308 may not be integrated onto the balloon surface in order to reduce manufacturing cost and complexity. The expandable member 306 and sensing elements 308, instead, may be separate members coupled to one another by mechanisms known in the art. For example, sensing elements 308 may be arranged and spaced along a plurality of flexible wires, filaments, or the like, that are attached or otherwise gathered together at their proximal and distal ends. A balloon may be placed inside the arrangement of filaments, and, as the balloon is expanded, the balloon may contact the filaments and force them and the sensing elements 308 against the inner wall of the stomach.

Sensing elements 308 may be electrical, mechanical or optical in nature. When mechanical in nature, sensing elements 308 may be configured to measure the mechanical contact force applied against the stomach wall by expandable member 306. This measured force may be converted into digital data as the sensing elements 308 make contact with the mucosal side of the stomach wall. The mechanical contact force data may displayed at a control panel, e.g., at a display of interface device 205. Furthermore, a contact force threshold may be utilized to guide a selective measurement of the gastric electrical signals. When a measured contact force reaches a designated value (e.g., the contact force threshold), hardware device 204 may begin recording mucosal electrical signals. Tying a minimum force threshold to recording of electrical measurements by the sensing elements 308 may improve efficiency and recording quality by ensuring that sensing elements 308 are in sufficient contact with mucosal tissue. For example, in ablative or other therapies, once optimal electrode and tissue contact is confirmed, ablative or therapeutic energy may be delivered according to the contact force that is indicative of electrode and tissue contact, ensuring optimal and safe energy delivery parameters are selected. In some examples, sensing elements 308 may be electrical (electrophysiology) sensors. The contact force could be obtained by analyzing the value of the electrode/tissue impedance. The electrode contact force also can be obtained via an array of optical sensors or mechanical sensors. The optimal range of the impedance value may indicate the optimal tissue contact that leads efficient resistive tissue heating and lower the risk of tissue charring and perforation.

Mapping device 300 also may be configured to allow a medical practitioner to mark areas in the stomach for subsequent treatment or follow-up mapping and monitoring. In one example, mapping device 300 may include one or more needles configured to inject a dye (e.g., a fluorescent dye) to selected locations within the body. Mapping device 300 may include one hollow needle or delivery device adjacent to each sensing element 308, such that when any given sensing element 308 identifies a physiological event or location of interest (e.g., the location of a gastric dysrhythmia), mapping device may be configured to deliver dye to that location. In one example, the dye may fluoresce when a black light is applied within the body. The dye may be injected into the serosal layer of stomach or in any other suitable location. In other examples, the dye may include carbon particles or India ink.

Figure 4:
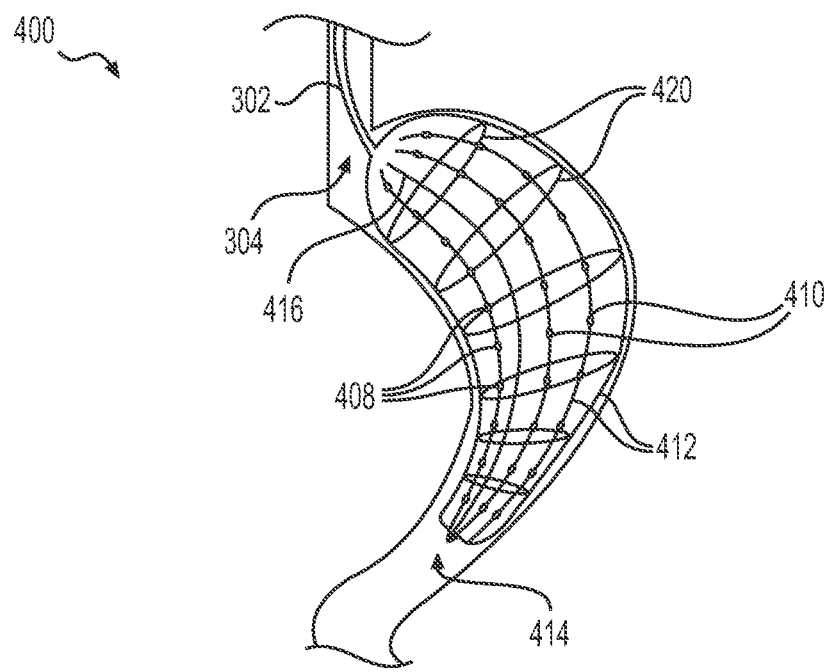

FIG. 4 illustrates an example of a mapping device 400. Mapping device 400 may include an expandable basket 410 having a plurality of legs 412, at distal end 304 of catheter 302. Each of the plurality of legs 412 may be configured to converge toward an atraumatic distal tip 414 of expandable basket 410. Each leg 412 may include a plurality of sensing elements 408. The sensing elements 408 of a given leg 412 may be longitudinally spaced from one another. Accordingly, the sensing elements 408 may include, but are not limited to, band electrodes or dot electrodes formed on the surface of leg 412. Longitudinally spaced and adjacent sensing elements 408 on a given leg 412 may be insulated from one another such that the proximal and distal end of each sensing element 408 is defined by an electrically non-conductive material.

Each leg 412 may include any number of sensing elements 408. A lead (not shown) may be electrically coupled to each sensing element 408. The lead may extend through the catheter 302 toward hardware device 204. In some examples, legs 412 may include a resilient inert material, such as, e.g., Nitinol metal or silicone rubber. In the illustrated example of FIG. 4, expandable basket 410 includes five legs 412 that are radially spaced from one another at substantially equal intervals. It is contemplated that any other number of legs 412 may form expandable basket 410, and that legs 412 may be spaced from one another at uneven intervals.

The expandable basket 410 may be moved between a collapsed configuration and an expanded configuration using any suitable mechanism. For example, expandable basket 410 may be self-expandable and biased toward the expanded configuration such that expandable basket 410 may expand radially outward when urged from the distal end of catheter 302 (basket 410 may move relative to catheter 302 within a lumen of catheter 302). In contrast, expandable basket 410 may move to a collapsed configuration when the distal end 304 of catheter 302 is urged distally relative to expandable basket 410. Self-expansion may occur because basket legs 412 may be formed with a pre-set configuration from a material capable of being compressed to a generally compressed configuration without plastic deformation. Such materials may include, e.g., shape memory alloys, including, but not limited to, nitinol and elgiloy. As all basket legs 412 restore themselves to the expanded configuration, expandable basket 410 may expand until each leg 412 makes contact with a wall of a body lumen or cavity. In some examples, expandable basket 410 may have a preset shape corresponding to the interior of a stomach.

Mapping device 400 also may include an actuating member (e.g., a wire) 416 that may be coupled at a proximal end to actuator 222 (referring to FIG. 2). The actuating member 416 may extend through a lumen of catheter 302, through a volume defined by the plurality of legs 412, to the distal tip 414. Expandable basket 410 may be moved from the collapsed configuration to the expanded configuration by pulling actuating member 416 proximally. A medical practitioner may be able to control the amount of force that expandable basket 410 applies to the stomach wall based on the amount of force applied to actuating member 416. Actuating member 416 also may be configured to transmit electric current and/or measured data in some examples. Releasing actuating member 416 may cause the expandable basket 410 to return to the collapsed configuration.

Alternatively, actuating member 416 may be a rigid pushing member. In response to a distally applied force, the pushing member may push expandable basket 410 distally out of catheter 302, causing expandable basket 410 to spring radially outward into the second, expanded configuration. Other modes of expansion, such as expansion by employing a balloon device within expandable basket 410, may be employed as desired.

Mapping device 400 may include one or more circumferential ties 420 that extend circumferentially around the plurality of legs 412. Each circumferential tie 420 may be coupled to each leg 412 to help maintain legs 412 relatively equidistant from one another. Adjacent circumferential ties 420 may be longitudinally spaced from one another. Circumferential ties 420 may be formed from any suitable material. In one example, circumferential ties 420 include an elastic material, such as, e.g., silicone. However, other materials, such as nitinol, are also contemplated.

Figure 5:
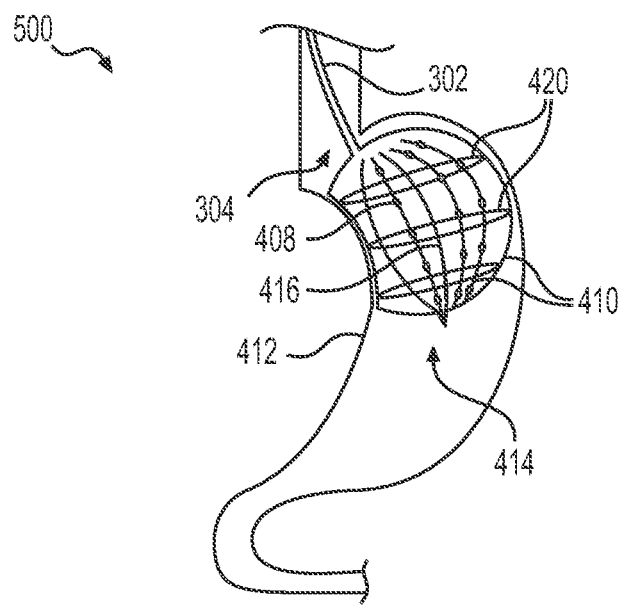

The mapping device 400 shown in FIG. 4 may be configured to map the electrical activity from the interior of the stomach without being repositioned. That is, mapping device 400 may be large enough, and include enough sensing elements 408 such that substantially all of the electrical activity of the stomach can be recorded without repositioning the mapping device 400. A substantially similar mapping device 500 is shown in FIG. 5. Mapping device 500 may be substantially similar to mapping device 400 except that mapping device 500 may be smaller, and thus may require repositioning and additional measurement steps to map a substantial entirety of the stomach.

Figure 6:
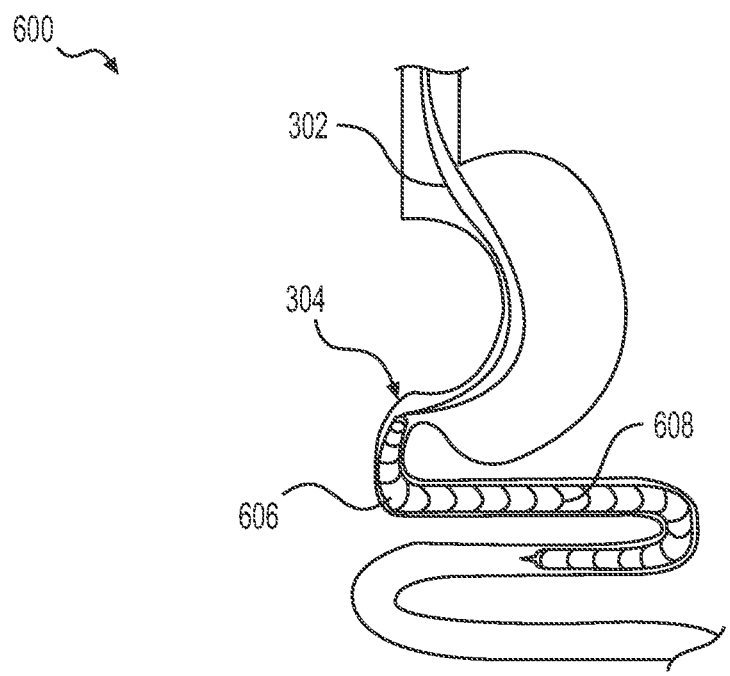

A mapping device 600 is shown in FIG. 6. Mapping device 600 may include a catheter 302, and an expandable member (e.g., a balloon) 606 extending from distal end 304 of catheter 302. Mapping device 600 may include a plurality of sensing elements 608 that are longitudinally spaced from one another. Sensing elements 608 may be circular band electrodes configured to both measure electrical activity within the duodenum and/or small intestine, and deliver therapeutic energy. Alternatively, instead of a plurality of band electrodes, mapping device 600 may include a matrix of sensing elements spaced about the outer surface of expandable member 606. The matrix may be formed by a plurality of rows of longitudinally spaced sensing elements. Each of the rows may be circumferentially spaced from adjacent rows. A given sensing element 608 of the matrix may be longitudinally spaced from one or more sensing elements 608, and also may be circumferentially spaced from one or more sensing elements 608.

Figure 7:
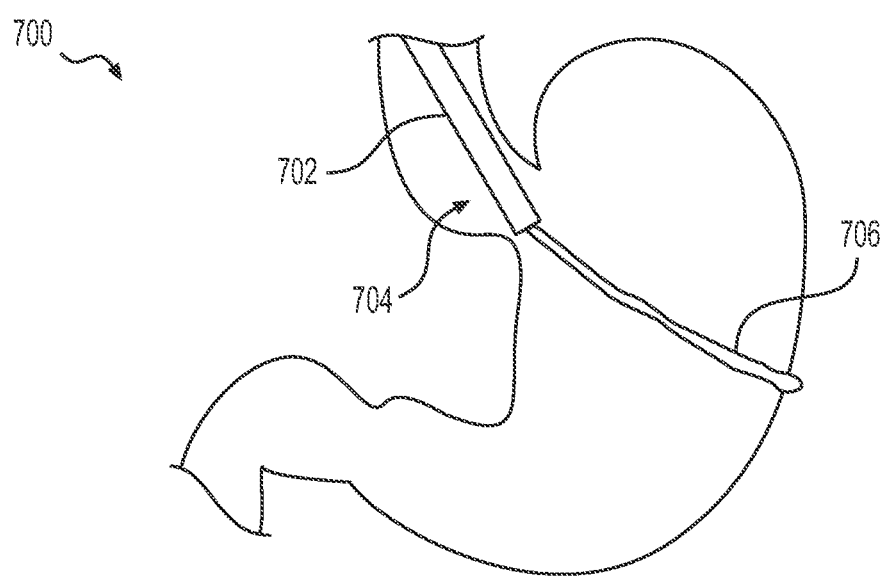

A medical device 700 is shown in FIG. 7. Medical device 700 may be used in conjunction with the mapping devices set forth above, or may be used separately. In some examples, medical device 700 may be the medical device 202 described with reference to FIG. 2, and may be controlled at least in part by hardware device 204. Medical device 700 may include an endoscopic member 702 extending from a proximal end (not shown) toward a distal end 704. A catheter 706 may extend distally from endoscopic member 702. In some examples, catheter 706 may include one or more features configured to help catheter 706 pierce through tissue. For example, a distal end of catheter 706 may include a needle point, an electrode, a cautery device, or another tool configured to pierce through tissue.

Figure 8:
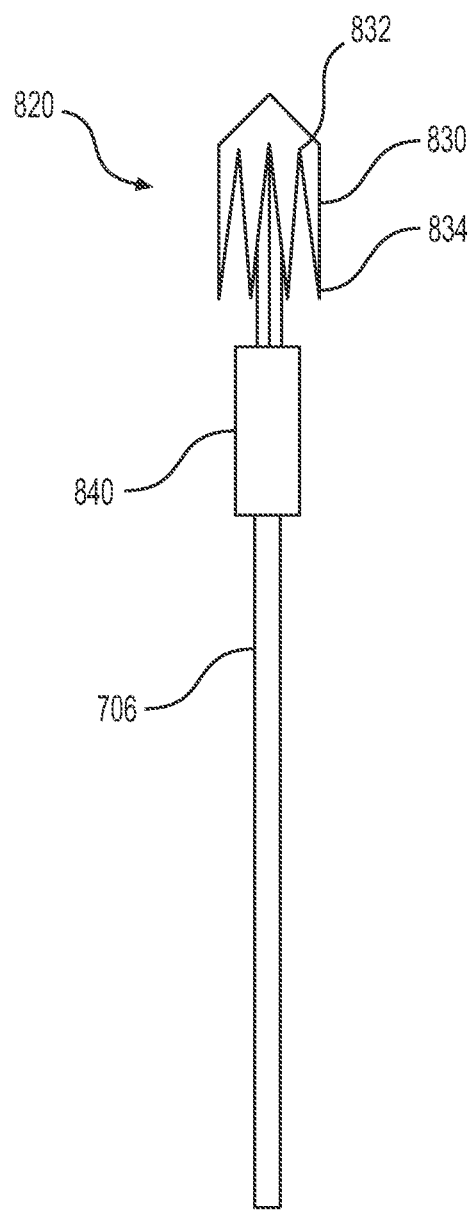
FIG. 8 is a side view of a device in a compressed configuration, according to an example of the present disclosure.

FIG. 8 illustrates one example of an umbrella-like expandable assembly disposed at the distal end of catheter 706. In this example, an expandable assembly 820 may be disposed at the distal end of catheter 706. A sliding plunger or expansion mechanism 840 may be slidable relative to the catheter 706. Expandable assembly 820 may include a plurality of legs or wire elements 830. Each of the wire elements 830 may have a proximal end 832 and a distal end 834. Proximal ends 832 of wire elements 834 may be connected to the distal end of the catheter 706. Wire elements 834 may be configured to deliver therapeutic energy (e.g., RF, electrical fields) to tissue in a monopolar or bipolar manner.

Figure 9:
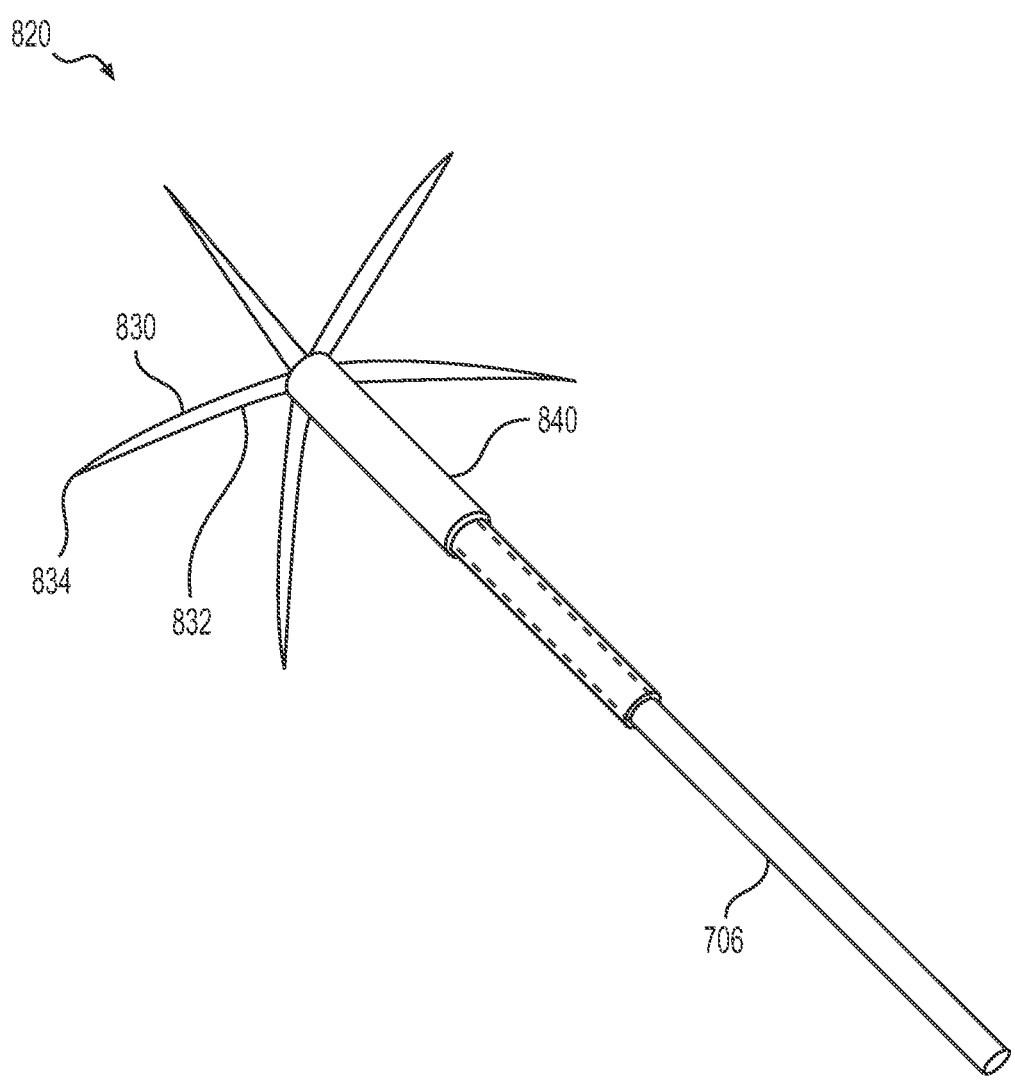
FIG. 9 is a perspective view of the device of FIG. 8 in an expanded configuration.

Expandable assembly 820 may be movable between an expanded configuration (shown in FIG. 9) and a collapsed position (shown in FIG. 8) as expansion mechanism 840 slides along the catheter 706, and back towards the proximal end of catheter 706. Specifically, the slidable plunger or expansion mechanism 840 may include a lumen that is sized to slidably receive a portion of catheter 706 therein. When expansion mechanism 840 is pushed distally along catheter 706 toward expandable assembly 820, the expansion mechanism 840 may push wire elements 830 to expand radially outwardly into the expanded configuration as shown in FIG. 9.

Figure 10:
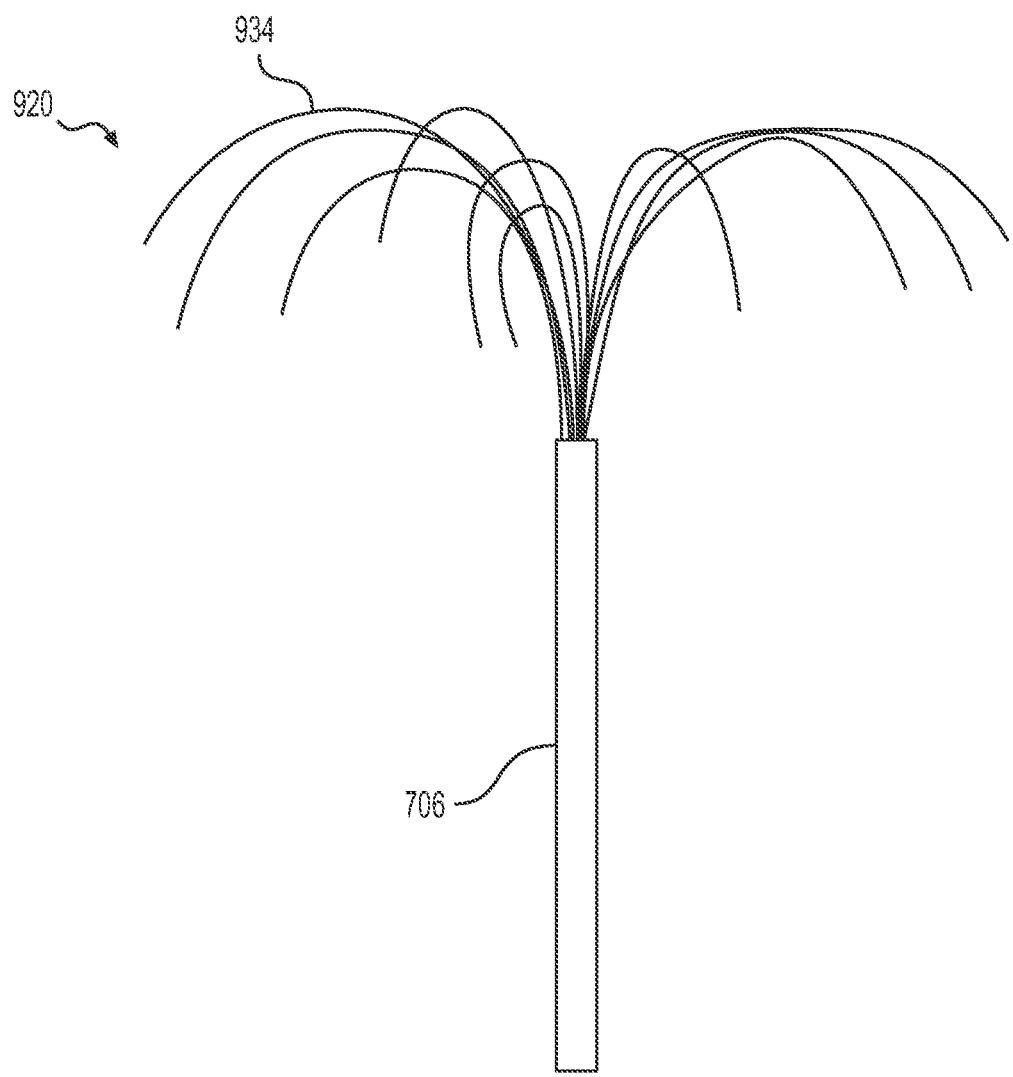

FIG. 10 depicts another example where a needle array 920 is disposed at the distal end of catheter 706. In this example, a plurality of electrically conductive wires 934 may extend distally from the distal end of catheter 706 when in a deployed configuration. Wires 934 may be bundled at their respective proximal ends, and may be separate from one another at their respective distal ends. In this example, catheter 706 may be electrically insulated or non-conductive.

Each wire 934 may arch once positioned outside of catheter 706, forming a "U" shape. Thus, array 920 may be formed of a plurality of wires 934 curving radially outwardly from a longitudinal axis of catheter 706. Wires 934 may be configured such that when fully extended past catheter 706, a portion of each wire 934 is perpendicular to the longitudinal axis of catheter 706, and may continue to curve such that distal ends of wires 934 are oriented generally parallel to the longitudinal axis of catheter 706. The array 920 may be deployed distally of a treatment site and retracted to allow the distal ends of the wires 934 to pierce through tissue. Piercing of tissue with the distal ends of wires 934 may enable more targeted delivery of RF therapy to, e.g., smooth muscle tissue disposed beneath surface tissues.

Catheter 706 is shown in FIG. 11 with a steerable section 1102 disposed at its distal end. A plurality of energy delivery elements 1104 may be disposed within the steerable section 1102, and/or along other portions of catheter 706. In some examples, catheter 706 may include a distally-facing energy delivery element 1104 at its distalmost point. The distally-facing energy delivery element may help catheter 706 pierce through tissue. Energy delivery elements 1104 may be substantially similar to sensing elements and electrodes described herein, or may have another suitable structure. A plurality of insulating or non-conductive regions 1106 may be disposed between adjacent energy delivery elements 1104.

In an alternative example, energy delivery elements 1104 may be active regions configured to reduce tissue temperature upon contact, while insulated regions 1106 may be zones having a negligible effect on tissue temperature upon contact. The insulated regions may be formed of an insulated material, such as, e.g., polymers (e.g., PTFE, PET, polyamides, or woven polymers), silicone, reflective coatings (foil, sputtered gold, chrome, aluminum or other metal), or any material that results in the surface temperature of the insulated regions being greater than that of the surface temperature of energy delivery elements 1104. In some examples, the separation of insulated regions and active regions may be achieved by the routing of cooled substances through catheter 706 in specific patterns, or by other suitable mechanisms. Channels for fluid flow may be formed from microtubing or laser etching of polymers, for example. In some examples, insulated regions may be formed by applying a low-conductive substance catheter 706 in a desired pattern.

The steering of steerable section 1102 may achieved by well-known steering mechanisms. For example, a flat, resilient center support member (not shown) may be positioned in an interior of catheter 706. The support member may be actuated e.g., pull wires having distal ends secured on opposing sides of the steering member.

FIG. 12 shows the distal end of catheter 706 having a spiral or coiled shape, along with energy delivery elements 1104 and insulating regions 1106 as described with reference to FIG. 11. The distal end of catheter 706 may be biased into the coiled configuration shown in FIG. 12. In other examples, catheter 706 may include a shape memory material, and may assume the coiled configuration after a suitable stimulus (e.g., temperature, chemical, or electrical) is applied. The coiled configuration may increase the surface area of catheter 706 that may be applied against tissues in confined spaces.

FIG. 13 shows a balloon 1326 disposed at the distal end of catheter 706 in an alternative example. Balloon 1326 may be inflated with an inflation fluid delivered by fluid delivery system 220 (referring to FIG. 2) via a lumen of catheter 706. The fluid within the balloon 1326 may be heated by an electrode 1328. The electrode 1328 is illustrated in the shape of a coil, but any other electrode shape also may be used. The electrode 1328 may be used as a resistance heater by application of an electric current to the electrode 1328. Alternatively, radio frequency or microwave energy may be applied to the electrode 1328 to heat the fluid within the balloon 1326. The heat then may pass from an exterior of the balloon 1326 to a targeted body tissue. The radio frequency or microwave energy also may be applied indirectly to body tissues through the fluid and the balloon. In such examples, both the fluid and the balloon 1326 may be formed from electrically conductive materials. In addition, hot fluid may be transmitted to the balloon 1326 from an external heating device for conductive heating of body tissues. In some examples, a distal end 1330 of balloon 1326 may include electrically insulating and/or thermally insulating materials in order to prevent tissues distal of balloon 1326 from receiving therapy.

FIG. 14 shows a balloon 1426 disposed at the distal end of catheter 706. Balloon 1426 may be inflated in a substantially similar manner as balloon 1326 described with reference to FIG. 13. One or more electrodes 1318 may be positioned on an exterior surface of inflatable balloon 1426. The electrodes 1318 may be electrically connected to hardware device 204 and energy generator 203 (referring to FIG. 2) by leads extending through the outer surface of balloon 1426, and through a lumen of catheter 706. Balloon 1426 may be filled with a fluid such as saline or air to bring electrodes 1318 into contact with body tissues. In one example, electrodes 1318 may be positioned only on a proximally-facing surface of balloon 1426. In another example, electrodes 1318 may be positioned only a distally-facing surface of balloon 1426.

A needle 1502 is shown extending from catheter 706 in the example of FIG. 15. As shown, needle 1502 may be configured to pierce through tissue to treat a target tissue layer 1501. Needle 1502 may be configured to deliver a suspension of microparticles or nanoparticles 1506 within the tissue layer 1501. The microparticles 1506 may be formed of conductive and/or bioabsorbable materials (e.g., magnesium), and may be heated by absorption of energy (e.g., RF energy) delivered by needle 1502 or by another suitable device. The micropoarticles may include iron microparticles that may be between 1 nm and 0.5 mm in diameter. The microparticles may be heated by an inductance heating method.

Hardware Device

Referring to FIG. 2, hardware device 204 may be coupled to a proximal end of a medical device 202 to receive, store, process, and/or control the data acquisition by the sensing elements of the medical device 202, and/or control the energy therapy delivered by the medical device 202. Hardware device 204 may include a memory, a battery (or other suitable element for powering hardware device 204), and/or a transceiver. Hardware device 204 may be connected to electronic network 200 through a cellular network and/or a Wi-Fi network. Thus, hardware device 204 may be configured to collect electrical data from a patient via medical device 202, and transmit collected electrical data over electronic network 200. Hardware device 204 also may have a web browser or mobile browser installed for receiving and displaying content from web servers, in addition to other components to facilitate operation, such as, e.g., start and stop buttons, keyboards, touch screens, and the like. Electronic network 200 may be the Internet, or any other combination of wired and/or wireless electronic networks.

Hardware device 204 may be operatively coupled to energy generator 203, fluid delivery system 220, actuator 222, and medical device 202. Hardware device 204 may be configured to optimize energy delivery to a patient based on algorithms and/or inputs from one or more sensing elements. In some examples, the hardware device 204 may include a processor that is generally configured to accept information from the system and system components, and process the information according to various algorithms to produce control signals for controlling energy generator 203, fluid delivery system 220, actuator 222, and medical device 202. The processor may produce information signals that may be directed to visual indicators, digital displays, audio tone generators, or other indicators of, e.g., interface device 205, in order to inform a user of the system status, component status, procedure status or any other useful information that is being monitored by the system. The processor may be a digital IC processor, analog processor or any other suitable logic or control system that carries out the control algorithms. The processor may be coupled to one or more non-transitory computer readable storage devices that may perform any of the actions described herein for operating medical device 202, including storing collected data, and transmitting data to server system 206 (to be described herein) via electronic network 200.

The controller may be configured to run a plurality of algorithms to prepare and control medical device 202 for data collection and/or therapeutic energy delivery. In some examples, hardware device 204 may be compatible with standardized equipment at hospitals or the like. The controller may be coupled to a bioamplifier, which may be used to increase the magnitude of signals received from sensing elements described herein.

Hardware device 204 may include or be coupled to a visual display (e.g., interface device 205) to assist a user during operation of hardware device 204. In some examples, hardware device 204 may be configured to show a progress of the data collection, indicate that data collection is complete, and/or indicate that transmission to server system(s) 206 is complete. In some examples, hardware device 204 may include error logs and solutions. In some examples, hardware device 204 may use error logs to alert the physician and other members of the clinical team to a problem. An error may indicate that a repositioning of medical device 202 is desired to obtain optimal data or to cause optimal therapy.

Hardware device 204 may be configured to allow a user to log into a doctor or hospital account and create patient profiles. Hardware device 204 may be configured to perform patient testing while offline or online, if desired.

Energy Generator

Energy generator 203 may be configured to apply voltages across sensing elements to produce electric fields. Energy generator 203 may be adapted, for example, to promote electrically assisted therapeutic agent delivery within a subject, including electroporation. Power sources and power application schemes for use in electroporation are known in the medical device art. Energy generator 203 may be configured to deliver irreversible or reversible electroporation therapies via electrodes disposed within a body lumen. In other examples, energy generator 203 may be configured to deliver radio frequency (RF) energy to sensing elements and/or electrodes of the present disclosure.

Fluid Delivery System

Fluid delivery system 220 may be a standard balloon inflation device and/or may include an inflation pump (not shown) that is in fluid communication with medical devices of the present disclosure. More specifically, activation of the pump by a user may cause the disclosed medical devices to be selectively moved between a deflated configuration and an inflated configuration, for example, when medical device 202 includes an inflatable balloon. The fluid delivery system 220 may include one or more heat exchange devices configured to add heat to or remove heat from the fluid to be circulated through a balloon.

Actuator

Actuator 222 may be any suitable automatic and/or user operated device in operative communication with energy generator 203, fluid delivery system 220, and/or medical device 202 via a wired or wireless connection, such that actuator 222 may be configured to enable activation of energy generator 203, fluid delivery system 220, and/or medical device 202. Actuator 222 may therefore include a switch, a push-button, computer or other suitable actuator configured to operate energy generator 203 and/or fluid delivery system 220. Further, actuator 222 may include a handle, slider, trigger, and/or other suitable mechanism configured to apply a force to an actuating member (e.g., actuating member 416 of FIG. 4) of a medical device.

Interface Device

In one example, each of the interface devices 205 may include a server, personal computer, tablet computer, mobile device, smartphone, and/or personal digital assistant ("PDA") disposed in communication with electronic network 200. For example, each of interface devices 205 may be a touchscreen enabled device, such as an Apple iPad, Samsung Galaxy, Amazon Kindle, Microsoft Surface, or any other equivalent or similar device. Each of interface devices 205 may have a web browser or mobile browser installed for receiving and displaying content from web servers. Thus, each of the interface devices 205 may be configured to receive and display data that is received and processed from hardware devices 204, over electronic network 200. For example, interface device 205 may receive output from the electronic network 200 and display it to the user. The output may include an identification of the location of certain gastric events or abnormalities, such as, e.g., the origin of a slow wave. The output also may include one or more recommendations for treatment.

In some examples, interface device 205 may implement appropriate security protocols, such as requiring the physician to enter logon credentials, so as to appropriately limit access to patient data and comply with regulations, such as the Health Insurance Portability and Accountability Act (HIPAA).

Server Systems

As shown in FIG. 2, a plurality of server systems 206, a browser web server 214, and/or a mobile web server 216 also may be disposed in communication with electronic network 200. In one example, server systems 206 may be configured to receive electrical data from hardware devices 204 over electronic network 200. Any of the devices or functionality of server systems 206, browser web server 214, and/or a mobile web server 216 may be combined together or separated, and may be operated by a single administrative entity, or outsourced to one or more other entities, such as a web hosting entity, web storage entity, and/or cloud computing service.

As shown in the example of FIG. 2, server systems 206 may include a data analyzer 210, which may analyze the received electrical data. Specifically, data analyzer 210 may be configured to analyze received electrical data for determining whether a given patient would be suitable for a particular clinical study, and/or for identifying potential obesity treatment locations, as will be described in more detail below.

Server systems 206 also may include one or more databases 208, where data analyzer 210 may be configured to store the received electrical data and/or the computed data. Any received data may be stored in the databases 208 in an encrypted form to increase security of the data against unauthorized access.

Server systems 206 also may include a health-care provider application program 212 that allows a physician or other health care provider to control parameters of the system, such as values used by the data analyzer 210 in the analysis. The application program 212 also displays data to the physician and allows the physician to select types of data to display, time periods of the data to display, levels of data detail to display and other operating parameters of the system. In response to a query by the physician, the application program 212 may fetch and display data from the databases 208.

As shown in FIG. 2, server systems 206 may be disposed in communication with a browser web server 214 and/or a mobile web server 216. Each of browser web server 214 and/or mobile web server 216 may be configured to interact with interface devices 205, such as to generate appropriate displays to facilitate user interaction with the application program 212. For example, browser web server 214 and/or mobile web server 216 may be configured to generate a window-metaphor based computer user interface on a screen of interface devices 205 or screen (not shown) coupled to the remote server systems 206, or the browser web server 214 and/or mobile web server 216 may generate web pages that are rendered by a browser or application of the interface devices 205. The interface devices 205 and the browser web server 214 and/or mobile web server 216 may communicate with each other using an appropriate encrypted protocol, such as Hypertext Transfer Protocol Secure (HTTPS).

Exemplary Method

Figure 16:
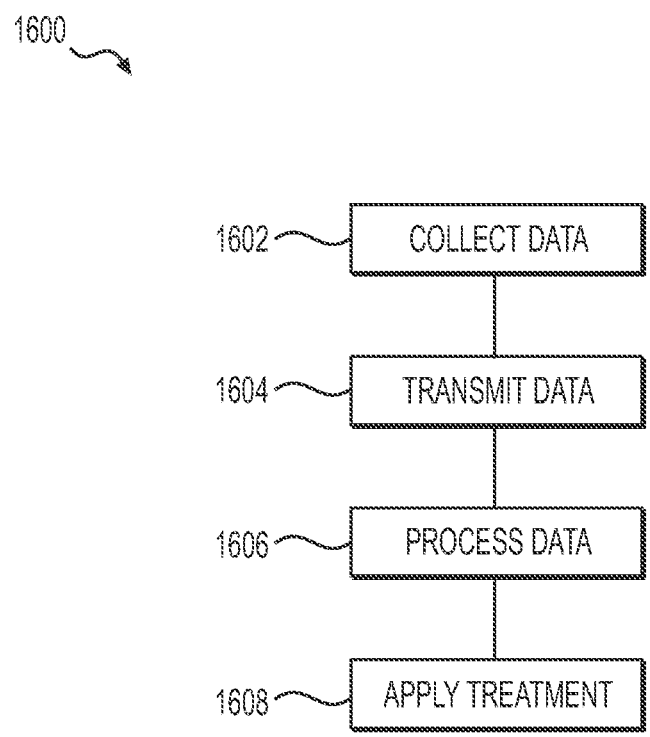
FIG. 16 is a flow chart of a method, according to an example of the present disclosure.

FIG. 16 is a flow diagram of a method 1600 for collecting, processing, and displaying electrical data, and for performing treatments using, e.g., the exemplary systems and devices of FIGS. 2-15. As shown in FIG. 16, method 1600 may initially include collecting electrical data from the gastrointestinal system of a patient (step 1602). For example, a physician may locate a mapping device (e.g., one of mapping devices 300, 400, 500, and 600) within the stomach of a patient, and collect electrical data over time. The presence of multiple sensing elements on the mapping devices disclosed herein also provides a spatial component to the electrical data. The disclosed sensing elements may thus be configured to generate an electrogram (e.g., an electrogastrogram) showing electrical data of a plurality of locations in the gastrointestinal system over time.

The electrograms may show the wave-like contractions of the stomach (peristalsis). Motility of the gastrointestinal tract may result from coordinated contractions of smooth muscle, which in turn derive from two basic patterns of electrical activity across the membranes of smooth muscle cells (slow waves and action potentials). Slow waves may be initiated by pacemakers, or the interstitial cells of Cajal (ICC). Slow wave frequencies may vary in the different organs of the gastrointestinal tract.

The electrical activity of the gastrointestinal tract can be subdivided into electrical control activity (ECA) and electrical response activity (ERA). ECA may be characterized by regularly recurring electrical potentials, originating in the gastric pacemaker located in the body of stomach. Further, a bradygastria may be a decreased rate of electrical activity in the stomach, while a tachygastria may be an increased rate of electrical activity in the stomach.

In some examples, hardware device 204 may receive a measurement of the force applied by each of a plurality of sensing elements against the stomach wall. Hardware device 204 may compare this measured force to a threshold force level. The threshold force level may be a minimum acceptable force necessary for collecting high-quality data. Hardware device 204 may not accept data recorded by the plurality of sensing elements until the measured force from each sensing element is above the minimum threshold level. Hardware device 204 may provide an indication, e.g., via a tone, light, or other indication that an expandable device should be expanded to a greater extent when the measured force at one or more sensing elements is below the minimum threshold. In some examples, hardware device 204 and its associated controller may automatically increase the expansion of an expandable member by, e.g., increasing the pressure to an expandable balloon, or by increasing a force applied to an actuating member of an expandable basket.

After hardware device 204 collects the required data, server system(s) 206 may receive electrical data from hardware device 204, which may then be stored in database(s) 208 (step 1604). The complete dataset of electrograms and other recorded information may be sent to the cloud for subsequent analysis.

At step 1606, the electrical data may be processed by data analyzer 210. In some examples, the collected data may be compared to animal models and/or patient models showing the characteristics that have been associated with various gastrointestinal disorders and treatments.

Data analyzer 210 may analyze electrograms generated based on data collected by medical device 202 and hardware device 204. For example, the electrograms produced by healthy patients may differ from those produced in obese patients. Electrograms and patterns also may differ between patients based on the type and/or severity of their condition. In some examples, data analyzer 210 may search for deviations, abnormalities, and/or dysrhythmias in the collected electrograms.

Analyzer 210 may interrogate each individual electrogram. In some examples, several thousand electrograms may be recorded during the course of study of a single patient, or another suitable number of electrograms may be recorded, if desired. In some examples, the output of the signals that have been observed in animal models and human patients may be compared to the individual patient under study.

In some examples, a database of collected data and correlations may be generated. The predictive capability of the database may increase as the database grows. Additional data may be input to data analyzer 210 via hardware device 204, interface device 205, or via another input mechanism, such as, e.g., a hospital input terminal or a patient database entry website that communicates with data analyzer 210 via electronic network 200. The database may include patterns of electrical data and information regarding that data that can be used to diagnose a new set of measured data. For example, measured electrical data from a mapping device may be compared by analyzer 210 to the database of electrical data, and analyzer 210 may be able to identify gastric events or abnormalities from the measured electrical data based on the comparison. In particular, the comparison may reveal that the measured electrical data has the same or similar pattern and/or shape as an electrogram stored in the database, and may provide a recommendation for treating the patient based on a treatment associated with the stored electrogram. The database also may include simulated electrograms input by a medical practitioner, which would correspond to a particular event and/or treatment. The simulated electrograms would allow analyzer 210 to still make a recommendation for a certain set of measured data even if the measured data set did not align well with an electrogram recorded from an actual patient and treatment. In some examples, analyzer 210 or a medical practitioner may be able to identify the slow wave, source of slow wave, and any other abnormal activity from the recorded electrical data. The baseline gastric myoelectric activities in humans could be recorded via said catheters, while the dominant frequencies normally were around 4 and 5 cycles per minute (CPM). The direction of slow wave propagation usually is from the proximal part (Corpus) to distal part of the stomach (Antrum). The abnormal gastric myoelectric activities could rise from different areas of the stomach in addition to the pacemaker area. In addition, these abnormal gastric myoelectric activities could have a faster rhythm, tachygastria, or a much slower rhythm, bradygastria.

Abnormal data may be different from baseline or general population data, and having this information/data may allow for alternatives therapies, such as bariatric surgery for patients who do not have a slow wave abnormality. For patients who do have a slow wave abnormality, pharmacotherapy or gastric resection may be recommended. Analyzer 210 or the medical practitioner may suggest treatments relevant for the identified conditions, such as, e.g., obesity, gastric motility disorders and/or gastric dysrhythmias.

The data analyzer 210 may determine the origin or location of the gastric pacemaker and rhythm, according to a predetermined algorithm or by comparing the recorded electrogram to a database of collected electrograms corresponding to known obesity conditions. The database may be continuously updated as new measurements, diagnoses, and treatments are uploaded to the database. Using this data and comparison, the data analyzer 210 may suggest treatment locations. Thus, devices of the present disclosure may include multi-channel recording systems that are able to detect with high sensitivity, low amplitude gastric electrical activities of the gastrointestinal tract, and are able to identify the conduction direction of these electrical activities on the mucosal side of the gastrointestinal system.

In some examples, analyzer 210 may be located within the hardware device 204, and the comparison may be performed locally on the hardware device 204. In such examples, the database may be transmitted from server 206, over electronic network 200, to hardware device 204.

From step 1606, method 1600 may proceed to step 1608, where a therapy may be performed using one or more of the devices disclosed herein.

In one example, endoscopic mapping and ablation may occur around the gastric pacemaker for an obesity treatment. Once a particular treatment area is determined based on the results of the mapping, the analyzer 210, or the medical practitioner, may direct a therapy to those particular treatment areas. In some examples, when a particular treatment area is identified based on the analysis of electrical data gathered by, e.g., devices 300, 400, 500, or 600, the same device may be used to deliver a therapy to those particular treatment areas. For example, a medical practitioner, or the data analyzer 210, may determine that certain sensing elements/electrodes should be activated to provide a therapy to a targeted region. That is, the analyzer 210 or the medical practitioner may use the mapping device to deliver a therapy to an identified treatment area. For example, the analyzer 210 or medical practitioner may determine that a particular sensing element is closest to the gastric pacemaker (or another suitable location to be treated), and without moving the mapping device from its recording position, may deliver therapy using that given electrode. It is further contemplated that additional sensing elements or electrodes adjacent or proximate to the given sensing element also may be activated to deliver the therapy.

After energy delivery, e.g., ablation, an electronic stimulator may be implanted to help regulate the electric activity of the gastrointestinal tract. The electronic stimulator may be similar to cardiac pacemakers, and may include an electrode configured to deliver an electrical pulse. In some examples, the electric activity of the gastrointestinal tract may be substantially eliminated so that post-treatment electrical activity is entirely regulated by the implanted electronic stimulator.

In other examples, the identified treatment areas, or areas corresponding to particular gastric locations (e.g., the origin of a slow wave) may be marked by the mapping devices. For example, an area of interest proximate to a particular sensing electrode may be marked by a needle or delivery device with a fluorescent dye as set forth above, so that the location can be easily identified for a subsequent treatment or analysis.

In some examples, Botox or another suitable chemical agent may be injected at or around the identified treatment area. In some examples, a medical practitioner may inject the agent into a location that was marked with a fluorescent dye by one of the mapping devices of the present disclosure. The chemical agent may be delivered in gel form and/or may be delivered into a bolus proximate the treatment site in order to give the agent additional time in which to act on the targeted treatment location. In some examples, chemical ablation methods may be permanent. By using a chemical agent (e.g., Botox), the gastric pacemaker may be reduced or knocked out over a extended time period (e.g., three months). Botox is a neurotoxin, and will interfere with electrical signals from the gastric pacemaker. Gastric myoelectric activities may also be inhibited using agents, e.g., epinephrine, glucagon and glutide. Application of those agents may diminish the gastric myoelectric activity was diminished and reduce the amplitude of gastric myoelectric activity. The gastric myoelectric activities could be provoked using a prokinetic agent such as metoclopromide. Furthermore, the gastric myoelectric activities could be induced from an electrical inactive state after the application of prokinetic agent.

In some examples, mechanical treatment or modification of tissue may be utilized to disrupt the gastric pacemaker. In such examples, the efferent nerves originating from the pacemaker may be cut or severed by making multiple linear and horizontal cuts around the gastric pacemaker at or near the level of the Myenteric plexus of Auerbach. Such a treatment may disrupt smooth muscle activity in the GI system.

The advantage gained by mapping the electric activity of the gastrointestinal tract is the localization of a specific area to deliver a targeted intervention. This localization may improve clinical outcomes of, e.g., Botox therapies and stimulation therapies for obesity by allowing for more precise targeting of desired treatment areas.

In some examples, treatments at step 1608 may be designed to inhibit stomach function by interfering with peristalsis, and by reducing the extensibility of the fundus. Thus, step 1608 may include methods to ablate the stomach wall to impair peristalsis, gastric accommodation, the myoelectric activity of the stomach, and ghrelin production to induce early satiety in patients with obesity. Ablation of the stomach muscle layers may interfere with gastric myoelectric activity, and thus the stomach's ability to expand to accommodate food, and contract for peristaltic motion. The damage caused from ablation may result in the formation of fibrotic tissue, which may alter the extensibility of the stomach wall, and thus its ability to expand and contract.

Step 1608 also contemplates any suitable form of ablation, such as, e.g., radiofrequency, laser, microwave, ultrasound, ionizing radiation, infrared, ultraviolet, cryoablation, chemical ablation, photodynamic therapy, and microsphere injection with remote heating. Ablation may be performed endoscopically in the fundus of the stomach to target the gastric mucosa, the stomach muscles, the vagus nerve, or any of its subsidiaries and the submucosal and myenteric plexuses.

In one example, the fundus of the stomach may be targeted in combination with a drug or drugs taken by the patient in order to affect hormonal production and release to enhance satiety. The weakened stomach smooth muscle may result in delayed gastric emptying and enhanced satiety. If satiety is achieved, a person with obesity may lose weight by eating less because they may feel satiated earlier.

It may be desirable to protect the mucosa inside the stomach, because the mucosa protects the stomach from the corrosive gastric environment, and ablating the gastric mucosa may create ulcers. In some examples, a patient may be prescribed symptom-reducing medications for the resultant ulcers during the timeframe for mucosal regeneration. It is also possible that ablation or treatment of the fundus may not result in ulcers, and/or that ulcers in the fundus may be asymptomatic.

In some examples, cooling fluids (e.g., cooled saline, cooled sterile water, or other fluids), may be applied to the mucosa of the stomach simultaneous with energy delivery. Thus, examples of the disclosure may include an additional step of reducing or stabilizing the temperature of mucosa or other tissue adjacent to where energy is being applied. This may be accomplished for example, by injecting a cold fluid into the stomach. The fluid may be sterile normal saline, or any other bio-compatible fluid. One benefit of reducing or stabilizing the temperature of the mucosa may be to prevent excessive destruction of the mucosa, or prevent irreversible destruction of the mucosa. In some cases, the application of a cooling fluid may substantially prevent any damage to the mucosa, reducing the risk for post-treatment ulcers to form. When a balloon is employed to deliver treatment, a fluid cooled by fluid delivery system 222 may be circulated through the balloon before, during, and/or after energy delivery to minimize damage to the mucosa, or to prevent damage to the mucosa entirely.

Some ablations of the gastric mucosa may reduce the hunger-producing hormone, ghrelin. Another exemplary therapy includes ablating the gastric mucosa in conjunction with the application of ghrelin antagonists that dampen or block ghrelin receptors in the body.

An alternative example includes ablating the stomach wall but sparing the mucosal lining. There are three layers of stomach muscle (longitudinal, circular, and oblique), which are located before the serosa. Ablation can be done using natural orifice transluminal endoscopic surgery (NOTES) from an interior of the stomach, through the stomach wall, to the exterior of the stomach. For example, as shown in FIG. 7, an endoscopic member 702 may be inserted through the nose or mouth of the patient, down the esophagus, and into the stomach. Catheter 706 may be extended distally from endoscopic member 702 to create an opening through the stomach wall. In some examples, catheter 706 may itself create the opening. In other examples, catheter 706 may only provide a treatment device suitable for providing the obesity therapy, and another device may be used to create the opening. In yet other examples, catheter 706 may be used to create the opening and may be used to deliver the obesity treatment. Approximately 5 mm (e.g., the thickness of the stomach wall) may need to be punctured to create the opening. Once the opening is created, catheter 706 may be extended through the opening to a volume exterior to the stomach (e.g., in the abdominal cavity). Once the distal end of the catheter is extended through the opening, a suitable treatment device (e.g., those depicted in FIGS. 8-14) may be expanded or otherwise deployed onto the exterior surface of the stomach to deliver a therapy. The application of therapeutic energy from the exterior surface of the stomach may minimize damage to the inner mucosal surface of the stomach.

The vagus nerve or any of its afferent subsidiaries also may be ablated at step 1608. The vagus nerve may be the primary neural conduit between the gastrointestinal system and the brain, interfacing cerebral commands to the release of hormones or muscular contractions. There are numerous vagal afferents throughout the stomach in the myenteric plexus that may be targeted for therapy. These afferents may be responsible for detecting the volume of ingested food via stretch and tension, and also may be responsible for detecting hormones in the gastric mucosa.

A truncal vagotomy or a total vagotomy may be performed with one or more devices of the present disclosure. In other examples, a neural ablation may be performed to cause sufficient damage to replicate a vagotomy. Treatments disclosed herein may ensure that the vagus nerve does not regenerate, and that vagus nerve ablation does not result in gastroparesis.

Step 1608 also may include targeted ablation of the smooth muscle layer of the stomach by injecting microspheres into the smooth muscle layer, and ablating those microspheres with a needle positioned in the smooth muscle layer, and not into the submucosal layer. In other examples, the submucosal layer also may be ablated. This therapy, shown by way of example in FIG. 15, may produce the desired effects on obesity while sparing the mucosal lining of the stomach.

In another example, microspheres may be delivered vascularly, or through the bloodstream into the smooth muscle layer. That is, microspheres may be injected either downstream of the target or systemically, followed by induction heating methods to ablate the sub-mucosa.

It will be apparent to those skilled in the art that various modifications and variations can be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only. The following disclosure identifies some other examples.

We claim:

1. A system for treating a gastrointestinal tract, comprising:
    a device configured to measure electrical activity at a plurality of locations within the gastrointestinal tract of a patient; and
    a controller configured to:
        compare the measured activity from the plurality of locations to a database of electrical activity corresponding to one or more gastric events, abnormalities, or dysrhythmias, wherein the controller is configured to receive the database, over an electronic network, from a server;
        determine one or more treatment locations based on the comparison; and
        cause the device to deliver therapy to the one or more treatment locations.

2. The system of claim 1, wherein the device includes a plurality of sensing elements that are longitudinally and circumferentially spaced apart from one another, wherein each of the plurality of sensing elements is configured to measure electrical activity from one of the plurality of locations within the gastrointestinal tract.

3. The system of claim 2, wherein each of the plurality of sensing elements is an electrode configured to deliver radiofrequency energy.

4. The system of claim 3, wherein determining the one or more treatment locations includes selecting one or more of the plurality of sensing elements to deliver radiofrequency energy to the gastrointestinal tract.

5. The system of claim 4, wherein causing the device to deliver therapy to the one or more treatment locations includes delivering radiofrequency energy to tissue with only the one or more selected sensing elements of the plurality of sensing elements.

6. The system of claim 5, wherein the device is configured to measure a force applied by each of the plurality of sensing elements against a wall of the stomach.

7. The system of claim 6, wherein the controller is configured to compare the measured force applied by each of the plurality of sensing elements to a threshold force level.

8. The system of claim 7, wherein the controller compares the measured electrical activity from the plurality of locations to the database of electrical activity only when the force applied by each of the plurality of sensing elements is above the threshold force level.

9. The system of claim 7, wherein the controller is configured to provide an indication that the device should be expanded to a greater extent when the force applied by one or more of the plurality of sensing elements is below the threshold force level.

10. The system of claim 1, further including a fluid delivery system configured to cool a volume of liquid, wherein the device includes a balloon, and the fluid delivery system is configured to deliver the cooled liquid to inflate the balloon.

11. The system of claim 1, wherein the one or more gastric events, abnormalities, or dysrhythmias include an origin of a slow wave.

12. The system of claim 1, wherein the database includes patterns of simulated electrical activity.

13. The system of claim 1, wherein the database includes electrical activity recorded from other patients.

14. The system of claim 1, wherein the server is configured to receive electrical data measured by different expandable devices via the electronic network, and is configured to update the database after receiving electrical data from the different expandable devices.

15. A system for treating a gastrointestinal tract, comprising:
a device configured to measure electrical activity at a plurality of locations within the gastrointestinal tract of a patient, wherein the device includes a balloon;
a fluid delivery system configured to cool a volume of liquid, and the fluid delivery system is configured to deliver the cooled liquid to inflate the balloon; and
a controller configured to:
compare the measured activity from the plurality of locations to a database of electrical activity corresponding to one or more gastric events, abnormalities, or dysrhythmias;
determine one or more treatment locations based on the comparison; and
cause the device to deliver therapy to the one or more treatment locations.

16. The system of claim 15, wherein the one or more gastric events, abnormalities, or dysrhythmias include an origin of a slow wave.

17. A system for treating a gastrointestinal tract, comprising:
a device configured to measure electrical activity at a plurality of locations within the gastrointestinal tract of a patient, wherein the device includes:
a plurality of sensing elements that are longitudinally and circumferentially spaced apart from one another, wherein each of the plurality of sensing elements is configured to measure electrical activity from one of the plurality of locations within the gastrointestinal tract;
wherein each of the plurality of sensing elements is an electrode configured to deliver radiofrequency energy;
wherein the device is configured to measure a force applied by each of the plurality of sensing elements against a wall of the stomach; and
a controller configured to:
compare the measured activity from the plurality of locations to a database of electrical activity corresponding to one or more gastric events, abnormalities, or dysrhythmias;
determine one or more treatment locations based on the comparison, by selecting one or more of the plurality of sensing elements to deliver radiofrequency energy to the gastrointestinal tract; and
cause the device to deliver therapy to the one or more treatment locations, by delivering radiofrequency energy to tissue with only the one or more selected sensing elements of the plurality of sensing elements.

18. The system of claim 17, wherein the controller is configured to receive the database, over an electronic network, from a server.

19. The system of claim 18, wherein the server is configured to receive electrical data measured by different expandable devices via the electronic network, and is configured to update the database after receiving electrical data from the different expandable devices.

20. The system of claim 17, further including a fluid delivery system configured to cool a volume of liquid, wherein the device includes a balloon, and the fluid delivery system is configured to deliver the cooled liquid to inflate the balloon.

* * * * *